(12) United States Patent
Hwu

(10) Patent No.: US 6,835,810 B2
(45) Date of Patent: Dec. 28, 2004

(54) FUSION PROTEIN FOR USE AS VECTOR

(75) Inventor: Paul L. Hwu, Taipei (TW)

(73) Assignee: GeneShuttle Biopharma, Inc., Taiwan (CN)

(*) Notice: Subject to any disclaimer, the term of this patent is extended or adjusted under 35 U.S.C. 154(b) by 391 days.

(21) Appl. No.: 10/144,549

(22) Filed: May 13, 2002

(65) Prior Publication Data

US 2003/0211590 A1 Nov. 13, 2003

(51) Int. Cl.⁷ ................... C07K 14/195; C07K 14/245; C07K 14/16
(52) U.S. Cl. ...................... 530/324; 530/300
(58) Field of Search .................. 530/300, 324

(56) References Cited

U.S. PATENT DOCUMENTS

| | | | |
|---|---|---|---|
| 6,090,619 A | 7/2000 | Weissig et al. | 435/320.1 |
| 6,339,139 B1 | 1/2002 | Gu et al. | 530/300 |

FOREIGN PATENT DOCUMENTS

| CA | 2390104 | 5/2001 |
|---|---|---|

OTHER PUBLICATIONS

Becker–Hapak et al., "TAT–Mediated Protein Transduction into Mammalian Cells," *Methods* 24:247–256 (2001).

Fischer et al., "Cellular Delivery of Impermeable Effector Molecules in the Form of Conjugates with peptides Capable of Mediating Membrane Translocation," *Bioconjugate Chemistry* 12:825–841 (2001).

Ho et al., "Synthetic Protein Transduction Domains: Enhanced Transduction Potential in Vitro and in Vivo," *Cancer Research* 61:474–477 (2001).

Izumi et al., "Y box–binding protein–1 binds preferentially to single–stranded nucleic acids and exhibits $3' \rightarrow 5'$ exonuclease activity," *Nucleic Acids Research* 29:1200–1207 (2001).

Wang et al., "Acquisition of double–stranded DNA–binding ability in a hybrid protein between *Escherichia coli* CspA and the cold shock domain of humain YB–1," *Molecular Microbiology* 38:526–534 (2000).

Graumann, et al. "A superfamily of proteins that contain the cold–shock domain", Tibs Trend in Biochemical Science, vol. 23, pp. 286–290 (1998).

*Primary Examiner*—Robert A. Wax
(74) *Attorney, Agent, or Firm*—McDonnell Boehnen Hulbert & Berghoff LLP

(57) ABSTRACT

The present invention provides a fusion protein comprising a fusion protein for delivery of a desired molecule into cells or nuclei, comprising i) a cold shock domain and the homologue or the functional equivalent derivatives thereof and ii) a membrane translocation sequence or the functional equivalent peptides and/or derivatives thereof. The fusion protein is used as a vector for nucleic acids delivery in vitro and particularly in vivo for gene therapy and the production of transgenic animal.

21 Claims, 8 Drawing Sheets pCDNA3.1/iTAT  PEGFP-N1/iTAT

Light microscope

Fluorescent microscope

```
                            SEQUENCE LISTING

<160> NUMBER OF SEQ ID NOS: 31
<210> SEQ ID NO 1
<211> LENGTH: 16
<212> TYPE: PRT
<213> ORGANISM: Drosophila melanogaster

<400> SEQUENCE: 1

Arg Gln Ile Lys Ile Trp Phe Gln Asn Arg Arg Met Lys Trp Lys Lys
1               5                   10                  15

<210> SEQ ID NO 2
<211> LENGTH: 16
<212> TYPE: PRT
<213> ORGANISM: Artificial Sequence
<220> FEATURE:
<223> OTHER INFORMATION: Retro-inverso pAntp (43-48)
<220> FEATURE:
<221> NAME/KEY: MISC_FEATURE
<223> OTHER INFORMATION: Reverse sequence of pAntp (43-58); Penetratin

<400> SEQUENCE: 2

Lys Lys Trp Lys Met Arg Arg Asn Gln Phe Trp Val Lys Val Gln Arg
1               5                   10                  15

<210> SEQ ID NO 3
<211> LENGTH: 16
<212> TYPE: PRT
<213> ORGANISM: Artificial Sequence
<220> FEATURE:
<223> OTHER INFORMATION: W/R Penetratin
<220> FEATURE:
<221> NAME/KEY: MISC_FEATURE
<223> OTHER INFORMATION: W/R Penetratin

<400> SEQUENCE: 3

Arg Arg Trp Arg Arg Trp Trp Arg Arg Trp Trp Arg Arg Trp Arg Arg
1               5                   10                  15

<210> SEQ ID NO 4
<211> LENGTH: 7
<212> TYPE: PRT
<213> ORGANISM: Drosophila melanogaster

<400> SEQUENCE: 4

Arg Arg Met Lys Trp Lys Lys
1               5

<210> SEQ ID NO 5
<211> LENGTH: 13
<212> TYPE: PRT
<213> ORGANISM: Human immunodeficiency virus
<220> FEATURE:
<221> NAME/KEY: MISC_FEATURE
<223> OTHER INFORMATION: HIV Tat

<400> SEQUENCE: 5

Gly Arg Lys Lys Arg Arg Gln Arg Arg Arg Pro Pro Gln
1               5                   10

<210> SEQ ID NO 6
<211> LENGTH: 11
```

```
<212> TYPE: PRT
<213> ORGANISM: Human immunodeficiency virus
<220> FEATURE:
<221> NAME/KEY: MISC_FEATURE
<223> OTHER INFORMATION: HIV Tat

<400> SEQUENCE: 6

Tyr Gly Arg Lys Lys Arg Arg Gln Arg Arg Arg
1               5                   10

<210> SEQ ID NO 7
<211> LENGTH: 7
<212> TYPE: PRT
<213> ORGANISM: Artificial Sequence
<220> FEATURE:
<223> OTHER INFORMATION: Protein Transduction Domain
<220> FEATURE:
<221> NAME/KEY: MISC_FEATURE
<223> OTHER INFORMATION: A synthetic protein transduction domain.

<400> SEQUENCE: 7

Arg Arg Arg Arg Arg Arg Arg
1               5

<210> SEQ ID NO 8
<211> LENGTH: 30
<212> TYPE: PRT
<213> ORGANISM: herpes simplex virus 1
<220> FEATURE:
<221> NAME/KEY: MISC_FEATURE
<223> OTHER INFORMATION: The minimum VP22 transduction domain consisting
      of the basic residues 267 to about 300.

<400> SEQUENCE: 8

Asp Ala Ala Thr Arg Ser Ala Ala Ser Arg Pro Thr Glu Arg Pro Arg
1               5                   10                  15

Ala Pro Ala Arg Ser Ala Ser Arg Pro Arg Arg Pro Val Glu
            20                  25                  30

<210> SEQ ID NO 9
<211> LENGTH: 17
<212> TYPE: PRT
<213> ORGANISM: Human immunodeficiency virus
<220> FEATURE:
<221> NAME/KEY: MISC_FEATURE
<223> OTHER INFORMATION: The fusion sequence of Gp41.

<400> SEQUENCE: 9

Gly Ala Leu Phe Leu Gly Trp Leu Gly Ala Ala Gly Ser Thr Met Gly
1               5                   10                  15

Ala

<210> SEQ ID NO 10
<211> LENGTH: 27
<212> TYPE: PRT
<213> ORGANISM: Artificial Sequence
<220> FEATURE:
<223> OTHER INFORMATION: Membrane fusion sequence.
<220> FEATURE:
<221> NAME/KEY: MISC_FEATURE
<223> OTHER INFORMATION: Fusion peptide sequence consisting of gp41
      fusion sequence and the SV40 NLS.

<400> SEQUENCE: 10

Gly Ala Leu Phe Leu Gly Phe Leu Gly Ala Ala Gly Ser Thr Met Gly
1               5                   10                  15

Ala Trp Ser Gln Pro Lys Ser Lys Arg Lys Val
```

<210> SEQ ID NO 11
<211> LENGTH: 27
<212> TYPE: PRT
<213> ORGANISM: Artificial Sequence
<220> FEATURE:
<223> OTHER INFORMATION: Membrane fusion sequence.
<220> FEATURE:
<221> NAME/KEY: MISC_FEATURE
<223> OTHER INFORMATION: Fusion peptide consisting of the Caiman crocody-
      lus Ig(v) light chain and the SV40 NLS.

<400> SEQUENCE: 11

Met Gly Leu Gly Leu His Leu Leu Val Leu Ala Ala Ala Leu Gln Gly
1               5                   10                  15

Ala Trp Ser Gln Pro Lys Lys Lys Arg Lys Val
            20                  25

<210> SEQ ID NO 12
<211> LENGTH: 12
<212> TYPE: PRT
<213> ORGANISM: Hepatitis B virus
<220> FEATURE:
<221> NAME/KEY: MISC_FEATURE
<223> OTHER INFORMATION: The HBV PreS2 antigen consisting of the translo-
      cation motif from residues 41-52.

<400> SEQUENCE: 12

Pro Leu Ser Ser Ile Phe Ser Arg Ile Gly Asp Pro
1               5                   10

<210> SEQ ID NO 13
<211> LENGTH: 12
<212> TYPE: PRT
<213> ORGANISM: Hepatitis A virus
<220> FEATURE:
<221> NAME/KEY: MISC_FEATURE
<223> OTHER INFORMATION: The HAV VP3 core protein.

<400> SEQUENCE: 13

Phe Trp Arg Gly Asp Leu Val Phe Asp Phe Gln Val
1               5                   10

<210> SEQ ID NO 14
<211> LENGTH: 25
<212> TYPE: PRT
<213> ORGANISM: Vesicular stomatitis virus
<220> FEATURE:
<221> NAME/KEY: MISC_FEATURE
<223> OTHER INFORMATION: The VSV-G peptide.

<400> SEQUENCE: 14

Lys Phe Thr Ile Val Phe Pro His Asn Gln Lys Gly Asn Trp Lys Asn
1               5                   10                  15

Val Pro Ser Asn Tyr His Tyr Cys Pro
            20                  25

<210> SEQ ID NO 15
<211> LENGTH: 20
<212> TYPE: PRT
<213> ORGANISM: Adenovirus

<400> SEQUENCE: 15

Ala Lys Arg Ala Arg Leu Ser Thr Ser Phe Asn Pro Val Tyr Pro Tyr
1               5                   10                  15

```
Glu Asp Glu Ser
            20

<210> SEQ ID NO 16
<211> LENGTH: 27
<212> TYPE: PRT
<213> ORGANISM: Artificial Sequence
<220> FEATURE:
<223> OTHER INFORMATION: Membrane fusion sequence.
<220> FEATURE:
<221> NAME/KEY: MISC_FEATURE
<223> OTHER INFORMATION: Synthetic or chimeric sequence.

<400> SEQUENCE: 16

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 17
<211> LENGTH: 18
<212> TYPE: PRT
<213> ORGANISM: Artificial Sequence
<220> FEATURE:
<223> OTHER INFORMATION: Membrane fusion sequence.
<220> FEATURE:
<221> NAME/KEY: MISC_FEATURE
<223> OTHER INFORMATION: Synthetic sequence from protegrins/procine
      leukocyte.

<400> SEQUENCE: 17

Arg Gly Gly Arg Leu Ser Tyr Ser Arg Arg Arg Phe Ser Thr Ser Thr
1               5                   10                  15

Gly Arg

<210> SEQ ID NO 18
<211> LENGTH: 16
<212> TYPE: PRT
<213> ORGANISM: Kaposi's sarcoma-associated herpesvirus
<220> FEATURE:
<221> NAME/KEY: MISC_FEATURE
<223> OTHER INFORMATION: Kaposi FGF signal sequence.

<400> SEQUENCE: 18

Ala Ala Val Ala Leu Leu Pro Ala Val Leu Leu Ala Leu Leu Ala Pro
1               5                   10                  15

<210> SEQ ID NO 19
<211> LENGTH: 12
<212> TYPE: PRT
<213> ORGANISM: Kaposi's sarcoma-associated herpesvirus
<220> FEATURE:
<221> NAME/KEY: MISC_FEATURE
<223> OTHER INFORMATION: Kaposi FGF signal sequence.

<400> SEQUENCE: 19

Ala Ala Val Leu Leu Pro Val Leu Leu Ala Ala Pro
1               5                   10

<210> SEQ ID NO 20
<211> LENGTH: 15
<212> TYPE: PRT
<213> ORGANISM: Homo sapiens
<220> FEATURE:
<221> NAME/KEY: MISC_FEATURE
<223> OTHER INFORMATION: Human integrin beta3 signal sequence.

<400> SEQUENCE: 20
```

Val Thr Val Leu Ala Leu Gly Ala Leu Ala Gly Val Gly Val Gly
1               5                   10                  15

<210> SEQ ID NO 21
<211> LENGTH: 30
<212> TYPE: PRT
<213> ORGANISM: Artificial Sequence
<220> FEATURE:
<223> OTHER INFORMATION: Membrane fusion sequence.
<220> FEATURE:
<221> NAME/KEY: MISC_FEATURE
<223> OTHER INFORMATION: Synthetic membrane fusion sequence

<400> SEQUENCE: 21

Val Ala Tyr Ile Ser Arg Gly Gly Val Ser Thr Tyr Tyr Ser Asp Thr
1               5                   10                  15

Val Lys Gly Arg Phe Thr Arg Gln Lys Tyr Asn Lys Arg Ala
            20                  25                  30

<210> SEQ ID NO 22
<211> LENGTH: 18
<212> TYPE: PRT
<213> ORGANISM: Artificial Sequence
<220> FEATURE:
<223> OTHER INFORMATION: Membrane fusion sequence.
<220> FEATURE:
<221> NAME/KEY: MISC_FEATURE
<223> OTHER INFORMATION: Model amphiphilic peptide.

<400> SEQUENCE: 22

Lys Leu Ala Leu Lys Leu Ala Leu Lys Ala Leu Lys Ala Ala Leu Lys
1               5                   10                  15

Leu Ala

<210> SEQ ID NO 23
<211> LENGTH: 30
<212> TYPE: PRT
<213> ORGANISM: Artificial Sequence
<220> FEATURE:
<223> OTHER INFORMATION: Membrane fusion sequence.
<220> FEATURE:
<221> NAME/KEY: MISC_FEATURE
<223> OTHER INFORMATION: Model amphiphilic peptide.

<400> SEQUENCE: 23

Trp Glu Ala Lys Leu Ala Lys Ala Leu Ala Lys Ala Leu Ala Lys His
1               5                   10                  15

Leu Ala Lys Ala Leu Ala Lys Ala Leu Lys Ala Cys Glu Ala
            20                  25                  30

<210> SEQ ID NO 24
<211> LENGTH: 35
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: Primer used to amplify CspA gene from E. coli.

<400> SEQUENCE: 24
gctagcatgt ccggtaaaat gactggtatc gtaaa                         35

<210> SEQ ID NO 25
<211> LENGTH: 26
<212> TYPE: DNA

```
<213> ORGANISM: Artificial Sequence
<220> FEATURE:
<223> OTHER INFORMATION: Primer
<220> FEATURE:
<221> NAME/KEY: misc_feature
<223> OTHER INFORMATION: Primer used to amplify CspA gene from E. coli.

<400> SEQUENCE: 25
ctcgagatta caggctggtt acgtta                                              26

<210> SEQ ID NO 26
<211> LENGTH: 38
<212> TYPE: DNA
<213> ORGANISM: Artificial Sequence
<220> FEATURE:
<223> OTHER INFORMATION: Reversed form of Tat peptide sequence (rTat).
<220> FEATURE:
<221> NAME/KEY: misc_feature
<223> OTHER INFORMATION: DNA encoding the DNA binding/NLS+/PTD, reversed
      form of Tat peptide sequence (rTat).

<400> SEQUENCE: 26
tatgggtcgc cgtcgtcaac gtcgtaaaaa gcgccgtt                                 38

<210> SEQ ID NO 27
<211> LENGTH: 40
<212> TYPE: DNA
<213> ORGANISM: Artificial Sequence
<220> FEATURE:
<223> OTHER INFORMATION: Reversed form of Tat peptide sequence (rTat).
<220> FEATURE:
<221> NAME/KEY: misc_feature
<223> OTHER INFORMATION: DNA encoding the DNA binding/NLS+/PTD, reversed
      form of Tat peptide sequence (rTat).

<400> SEQUENCE: 27
ctagaaccgc gcttttacg acgttgacga cggcgaccca                                40

<210> SEQ ID NO 28
<211> LENGTH: 59
<212> TYPE: DNA
<213> ORGANISM: Artificial Sequence
<220> FEATURE:
<223> OTHER INFORMATION: (SPKR)4
<220> FEATURE:
<221> NAME/KEY: misc_feature
<223> OTHER INFORMATION: Oligo that codes for the DNA condensation
      sequence, (SPKR)4.

<400> SEQUENCE: 28
tatgggctct cctaaacgct ctcctaaacg ctctcctaaa cgctctccta aacgtggtt          59

<210> SEQ ID NO 29
<211> LENGTH: 61
<212> TYPE: DNA
<213> ORGANISM: Artificial Sequence
<220> FEATURE:
<223> OTHER INFORMATION: (SPKR)4
<220> FEATURE:
<221> NAME/KEY: misc_feature
<223> OTHER INFORMATION: Oligo that codes for the DNA condensation
      sequence, (SPKR)4.

<400> SEQUENCE: 29
ctagaaccac gtttaggaga gcgtttagga gagcgtttag gagagcgttt aggagagccc         60
a                                                                         61

<210> SEQ ID NO 30
```

-continued

```
<211> LENGTH: 32
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(5)
<223> OTHER INFORMATION: n is a, c, g or t/u
<220> FEATURE:
<221> NAME/KEY: misc_feature
<223> OTHER INFORMATION: Complementary to partial coding sequence of
      CspA and PTD from TAT.

<400> SEQUENCE: 30
nnnnnggatc cagagaagtg tacgaacaca tc                                32

<210> SEQ ID NO 31
<211> LENGTH: 62
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(5)
<223> OTHER INFORMATION: n is a, c, g, or t/u
<220> FEATURE:
<221> NAME/KEY: misc_feature
<223> OTHER INFORMATION: Complementary to partial coding sequence of
      CspA and PTD from TAT.

<400> SEQUENCE: 31
nnnnnggatc ccgcaagaaa cgccgtcaac gccgcagagg atctctggac gaaggtcaga    60
aa                                                                  62
```

US 6,835,810 B2

FUSION PROTEIN FOR USE AS VECTOR

BACKGROUND OF THE INVENTION

1. Field of the Invention

The present invention relates to a fusion protein referred as a novel vector for delivering molecules into cells.

2. Description of the Prior Art

The transfer of genetic material into cells in mammals is of increasing therapeutic and commercial importance. For instance, gene therapy procedures are used to correct acquired and inherited genetic defects, cancer, and viral infection. The ability to express artificial genes in humans facilitates the prevention and/or cure of many major human diseases, including many diseases that are not amenable to treatment by other therapies. However, biological membranes are natural barriers central to compartmentalization in living systems. Therefore, the polypeptides and oligonucleotides are generally considered to be of limited therapeutic value. Many studies have been conducted to overcome the problem of delivering such polypeptides and oligonucleotides.

Most of the initial work focused on the use of retroviral vectors to transform these cells. However, numerous difficulties with retroviruses have been reported. For example, it is hard to infect certain cell types. Retroviruses typically enter cells via receptors and if such receptors are not present in the cell, or are not present in large numbers, the infection is not possible or efficient.

Many researchers developed liposome systems for delivering the polypeptides and oligonucleotides into the cells. Liposomes are small membrane-enclosed spheres that have been formed with the appropriate DNA entrapped within it. However, this system also has inherent problems. It is difficult to control the size of the liposome and hence the uniformity of delivery to individual cells. Additionally, it is difficult to prevent leakage of the contents of the liposome and as with other techniques, there is difficulty in directing cell-type specificity.

Recently, several small regions of proteins called protein transduction domains (PTDs) have been developed to transport molecules into cells (Fischer et al, Bioconjugate Chem., Vol. 12, No. 6, 2001). Such PTD can translocate the cell membrane freely in a way that is receptor-, or transporter-independent, non-saturable, and consumes no energy. The PTD can get across the barrier of the cell membrane within less than one hour. The fundamental requirements for the creation, isolation and utilization of TAT-fusion proteins to affect mammalian cells were described in Becker-Hapak et al. Methods 24, 247–256, 2001. In Steven et al., a series of synthetic PTDs that strengthen the α-helical content and optimize the placement of arginine residues were synthesized. Several PTD peptides possessed significantly enhanced protein transduction potential compared with TAT (Steven et al., Cancer Research 61, 474–477, Jan. 15, 2001). Furthermore, U.S. Pat. No. 6,090,619 described the preparation of a novel non-viral vector, which can bind to desired DNA to form a combination useful to transfect diseased mitochondria of human or animal cells. U.S. Pat. No. 6,339,139 provided a gene transfer system binding to a growth factor receptor, comprising a 4-element complex gene transfer system consisting of ligand oligopeptide/polycationic polypeptide/endosome release oligopeptide/exogenous DNA or 3-element complex consisting of ligand oligopeptide/polycationic polypeptide/exogenous DNA.

The delivery vector systems in the art were confronted with one or more obstacles as described below. First, the immune responses are elicited by viral vector and cationic liposome when they are injected into living animals. Second, the extra-cellular fluids of cells, like blood stream, may dilute or eventually digest the gene cargo, which results in the lost of gene to be delivered. Third, the phospholipid bi-layer of cell membrane forms a natural barrier against the entrance of the nucleotide molecules. Therefore, the large molecules like DNA gene cannot cross the cell membrane in a freely (active or passive) transportation way to deliver the foreign DNA gene cargo into the cells. Fourth, the gel-like cytoplasm is rich in proteases and/or nucleases milieus in which the DNA gene cargo was degraded by the mechanism of endosomal trapping. Fifth, the vector-DNA cargo in the cytoplasm of cell meets the second barrier—nuclear membrane. The DNA gene cargo should pass the nuclear membrane and release the DNA gene cargo in the nucleus where the gene can act. Sixth, even if the DNA gene cargo has ability to enter the cell nucleus, the delivery efficiency is low.

Based on the above obstacles, there is a need to develop a delivery system for effectively delivering a desired molecule into cells or nuclei.

SUMMARY OF THE INVENTION

The invention relates to a fusion protein for delivery of a desired molecule into cells or nuclei, comprising i) a cold shock domain and the homologue or the functional equivalent derivatives thereof and ii) a membrane translocation sequence or the functional equivalent peptides and/or derivatives thereof.

DETAILED DESCRIPTION OF THE INVENTION

Figure 1:
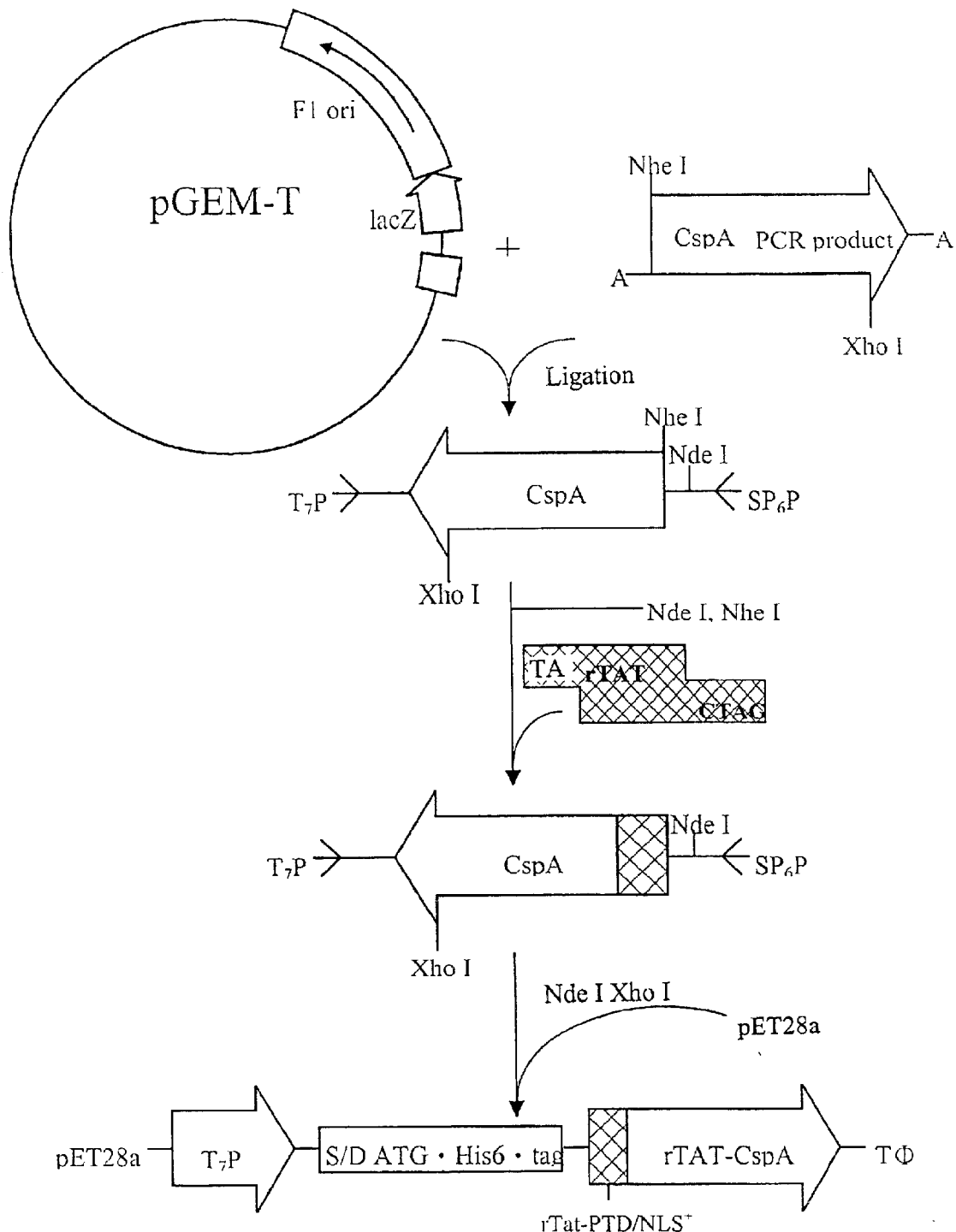
FIG. 1 shows the construction of gene that encodes the fusion protein of invention, rTAT-CspA, is represented by simplified flow-chart. The CspA gene is amplified from E. coli by PCR with primer 1 and 2, and gained the double stranded DNA/RNA binding activity by the insertion of annealed synthetic oligo 1 and 2 that encodes reversed form of TAT-PTD peptide sequence is introduced into the CspA gene and then the resulting of modified gene of the invention (rTAT-CspA) was subcloned into the pET28a expression vector.

The modem biotechnology is solely constructed on the basis of DNA gene delivery platform; for example, somatic cells gene therapy including cystic fibrosis, insulin-deficient diabetes and hemophilia A and B, etc. and transgenic animals. All of these research fields and commercial importance issues are required to ensure a more efficient, economic and safe gene delivery vector so as to achieve the goal of human healthcare improvement.

The present invention provides a new fusion protein used as a vector. The vector of the invention is a non-viral vector which can bind to desired nucleic acids and effectively delivery them into any organism such as animal, cell line and embryo. It can be produced in large quantity with the least amount of cost and broadly applied in various fields such as transgenic animal and gene therapy.

Recombiant Fusion Protein of the Invention

The "fusion protein" as used herein refers to a fusion of a first amino acid sequence encoding a target polypeptide with a second or more amino acid sequence(s) defining a domain (e.g. polypeptide portion) foreign to and not substantially homologous with any domain of a target protein.

The invention provides a fusion protein for delivery of a desired molecule into cells or nuclei, comprising i) a cold shock domain and the homologue or the functional equivalent derivatives thereof and ii) a membrane translocation sequence or the functional equivalent peptides and/or derivatives thereof.

Cold Shock Domain

According to the invention, any suitable cold shock domain and the homologue or functional equivalent derivatives thereof may be used in the fusion protein of the invention. The reason for choosing cold shock domain (CSD) is fully illustrated by its advantages: (1) the CSD is a universally conserved nucleic acid binding domain, prevalently existing in the pro- and eukaryotic kingdoms and as a result it contributes to minimizing the risk of immune response or even lower such risk to naught. Therefore, the CSD is the most proper candidate for the construction of gene delivery protein vector. Since the CSD does not cause large immune response of the host that received the gene delivery vector; (2) the intrinsic nucleic acid binding behavior of the CSD can be accommodated with the different Na+/K+ ions distribution in the outside and inside of a cell. It means that the CSD very likely will not lose the gene cargo during the process of delivery and achieve the high efficiency of gene delivery; and (3) recently Lescar et al. has proposed that the envelope glycoprotein of Alphaviruses, flaviviruses which adopt βbarrel-type structure to inserting the membrane of host cells and therefore, fusoqenic peptide in-frame fusion with CSD may escape from the endosomal trapping or fusing cellular membrane directly. (Lescar, J., Roussel, A., Wein, M. W., Navaza, J., Fuller, S. D., Wengler, G., Wengler, G., and Rey, F. A. (2001). The fusion glycoprotein shell of Semliki Forest virus: an icosahedral assembly primed for fusogenic activation at endosomal pH. Cell 105, 137–148. and Kuhn, R. J. et al. Cell 108, 717–725; 2002.)

The CSD has already been structurally well characterized, which refers to as anti-paralleled, 5 stranded beta-barrel structure which is denoted to the OB-fold. Therefore, the OB-fold family having the structure similar to the CSD can be used in the fusion protein of the invention. Many research results have indicated that the CSD is able to bind single stranded nucleic acids. For example, the RNP-1 and RNP-2 RNA binding motif and the phenylalanine, lysine residues on the peripheral surface of cold shock domain are responsible for single stranded DNA, RNA binding (Bycroft et al., Cell, Vol. 88, 235–242, Jan. 24, 1997). Izumi et al. indicated that the Y box-binding protein-1 binds single-stranded nucleic acids (Nucleic Acids Research, 2001, Vol. 29, No. 5, 1200–1207). Preferably, the cold shock domain is selected from the group consisting of CspA, CspB, CspC, CspD, rpl S1 RNA binding domain, the eukaryotic Y-box proteins, DNA binding Protein B (DBPB), DBPA, EF-1, mRNP3, mRNP4, FRG Y1, and nuclease-sensitive-element-binding protein 1 (NSEP 1). More preferably, the cold shock domain is selected from the group consisting of CspA, rpl S1 RNA binding domain, human YB-1 and DNA binding Protein B.

It will be understood that the CSDs of the invention are not limited to the above illustrated species but also include homologous sequences obtained from any other sources. According to the above disclosures, persons skilled in the art can realize that any CSD homologue capable of binding nucleic acids also can be used in the fusion protein of the invention.

According to the invention, the functional equivalent derivatives of the CSD and the homologue can also be used in the fusion protein of the invention. The CSD or the homologue thereof can be modified to bind double stranded nucleic acids. A "functional equivalent derivative" of the CSD and the homologue thereof includes molecules recombinantly produced or chemically synthesized polypeptides which function in a manner similar to the reference molecule to achieve a desired result. Thus, a functional equivalent derivatives of the CSD and its homologue encompasses derivatives including any single or multiple amino acid additions, substitutions and/or deletions occurring internally or at the amino or carboxy termini thereof, and including any modifications such as the insertion of DNA binding domain or DNA condensation domain. It has also been demonstrated that the CSD can be modified to be able to bind the double stranded DNA or RNA. For example, Wang et al. found that the modified cold shock domains of CspA by domain swapped with the positive charge amino acids from its eukaryotic counterparts YB-1 protein can result in gaining double-stranded DNA binding activity (Wang et al., Mol. Microbiology, 38(3): 526–534. 2000).

According to the invention, the CSD can be modified to obtain the derivatives having double-strand-RNA/DNA binding activity, which can be accomplished by inserting into the CSD either DNA condensation domain or DNA binding domain. The DNA condensation domain can bind more DNA and/or condense DNA molecule to form nucleosome-like structure which is resistant to DNase digestion thereby less fusion protein should be used. According to the invention, any suitable DNA condensation or binding domain that can modify clod shock domain/ribosomal protein S1 RNA binding domain to be bound to double stranded DNA, can be used in the invention. For example, the suitable DNA condensation or binding sequence is the DNA condensation domain (SPKR) 3–4 that is derived from histone, high mobility group (HMG) proteins or the nuclear localization sequences (NLS) that are rich with positive charge amino acid of arginine, lysine, such as SV40 large T antigen, Myc, YB1 protein and other putative NLS.

Membrane Translocation Sequence

According to the invention, the membrane translocation sequence of the fusion protein are those that possess the ability to transverse biological membranes efficiently in a process termed protein transduction, such as protein transduction domain (PTD) and membrane fusion sequence and their functional equivalent peptides or derivatives. It is known that the protein transduction does not occur through a classical reporter-, transporter- or endosome-mediated fashion. The membrane translocation sequence can rapidly and efficiently transduce molecules into cells. Examples of the membrane translocation sequence are shown in table below:

| Sequence | Name (origin of sequence) |
| --- | --- |
| Protein Transduction Domain | |
| RQIKTWFQNRRMKWKK (SEQ ID NO: 1) | Pantp (43–58) (Penetratin ®) |
| Kkwkmrrnqfwvkvqr (SEQ ID NO: 2) | Retro-inverso pAntp (43–58) |
| RRWRRWWRRWWRRWRR (SEQ ID NO: 3) | W/R Penetratin |
| RRMKWKK (SEQ ID No: 4) | Pantp (52–58) |
| GRKKRRQRRRPPQ (SEQ ID NO: 5) | HIV TAT |
| YGRKKRRQRRR (SEQ ID No: 6) | HIV TAT |
| rrrrrrr (SEQ ID No: 7) | R7 |
| Asp-Ala-Ala-Thr-Arg-Ser-Ala-Ala-Ser-Arg-Pro-Thr-Glu-Arg-Pro-Arg-Ala-Pro-Ala-Arg-Ser-Ala-Ser-Arg-Pro-Arg-Arg-Pro-Val-Glu (SEQ ID No: 8) | VP22 (267~300) |
| Membrane Fusion Sequence | |
| GALFLGWLGAAGSTMGA (SEQ ID NO: 9) | Gp41 fusion sequence |
| GALFLGFLGAAGSTMGAWSQPKSKRKV (SEQ ID NO: 10) | MPG (gp41 fusion sequence-SV40NLS) |
| MGLGLHLLVLAAALQGAWSQPKKKRKV (SEQ ID NO: 11) | Caiman crocodylus Ig(v) light chain-SV40NLS |
| PLSSIFSRIGDP (SEQ ID NO: 12) | PreS2-TLM |
| FWRGDLVFDFQV (SEQ ID NO: 13) | VP3 core protein |
| KFTIVFPHNQKGNWKNVPSNYHYCP (SEQ ID NO: 14) | VSV-G peptide |
| AKRARLSTSFNPVYPYEDES (SEQ ID NO: 15) | Ad fiber |
| GWTLNSAGYLLGKJNLKALAALAKKIL (SEQ ID NO: 16) | Transportan |
| RGGRLSYSRRRFSTSTGR (SEQ ID NO: 17) | SynB1 |
| AAVALLPAVLLALLAP (SEQ ID NO: 18) | MPS (Kaposi FGF signal sequence) |
| AAVLLPVLLAAP (SEQ ID NO: 19) | MPS (Kaposi FGF signal sequence) |

-continued

| Sequence | Name (origin of sequence) |
|---|---|
| VTVLALGALAGVGVG (SEQ ID NO: 20) | MPS (human integrin β3 signal sequence) |
| VAYISRGGVSTYYSDTVKGRFTRQKYNKRA (SEQ ID NO: 21) | P3 |
| KLALKLALKALKAALKLA (SEQ ID NO: 22) | Model amphiphilic peptide |
| WEAKLAKALAKALAKHLAKALAKALKACEA (SEQ ID NO: 23) | KALA |

One preferred embodiment of the invention is to provide a fusion protein for delivery of a desired molecule into cells or nuclei, comprising i) a cold shock domain and the homologue or the functional equivalent derivative thereof and ii) a membrane transduction domain. It is known in the art that the PTD can deliver the nucleic acids across cell membrane and nuclear membrane. By combining the CSD and PTD, the fusion protein of the invention can successfully deliver the desired nucleic acids to cytoplasma and cell nucleus. Studies have found a number of PTDs and their properties, features and efficacies (Fischer et al, Bioconjugate Chem., 2001, Vol. 12, No. 6, 825–841; Lindgren et al, Tips-March 2000, Vol. 21; Becker-Hapak et al, Methods 24, 247–256, 2001; and Ho et al, Cancer Research 61, 474–477, Jan. 15, 2001). For example, Tat is a transcription-activating factor of 86–102 amino acids in length, depending on the viral strain, and is involved in the replication of HIV. The minimum Tat transduction domain is the basic residues 49–57. The VP22, a 38-kDa structural protein from herpes simplex virus-1, has the remarkable property of intercellular transport. The minimum VP22 transduction domain is the basic residues 267–300. The Antp is the Drosophilae homeotic transcription factor, which is composed of three α-helices with a β-turn between helices 2 and 3. The third α-helix (residues 43–58) of the Antp is required for transduction.

Preferably, the PTD is selected from the group consisting of SEQ ID NOs. 1–8. More preferably, the PTD is selected from the group consisting of SEQ ID NOs: 1, 2, 4, 5, 6 and 7.

Another embodiment of the invention is to provide a fusion protein for delivery of a desired molecule into cells or nuclei, comprising i) a cold shock domain and the homologue or functional equivalent derivative thereof. It is also known in the art that membrane fusion sequence can translocate the molecules to the cell membrane. By combining the CSD and membrane fusion sequence, the fusion protein of the invention can deliver the desired nucleic acids to cytoplasma. To deliver the desired nucleic acids to the cell nucleus, the fusion protein should further comprise a nuclear localization sequence. For example, one representative membrane fusion sequence is PreS2-TLM. The PreS2 is a permeable peptide whose translocation motif is referred to as PreS2-TLM. The PreS2-TLM corresponds to an amphipathic α-helix between residues 41 and 52 of the PreS2 protein. The peptides appear to be able to penetrate a variety of cells including plant cells. Preferably, the membrane fusion sequence is selected from the group consisting of SEQ ID NO: 9–23. More preferably, the membrane fusion sequence is selected from the group consisting of 9, 10, 11, 12, 13, 17, 19, 20 and 21.

Protein Purification Tagged Sequence

According to the invention, the fusion protein can further comprise the protein purification tagged sequence. According to the invention, the purification tagged sequence is only an optional element of the fusion protein, which is just for protein purification. The fusion protein of the invention can be purified by chemical purification techniques. For example, the Tat-PTD containing protein can be purified by heparin column (Hakansson et al., Protein science (2001), 10:2138–2139. Furthermore, DNA column also can be used for the purification of the fusion protein of invention.

According to the invention, the protein purification tagged sequence can be N- or C-terminal fusion with gene delivery protein vector. Preferably, the protein purification tagged sequence is selected from the group consisting of HA, GST, His6 tag. More preferably, the protein purification tagged sequence is His6 tag.

Preparation of the Fusion Protein of the Invention

The fusion protein of the invention can be produced by culturing a host cell transformed with a recombinant vector under conditions allowing expression of said protein and isolating the protein thereby produced.

A DNA construct, i.e. recombinant DNA molecule, suitable for the expression of a fusion protein according to the invention may be used in the invention. For expression of a protein of the invention, the DNA construct is cloned into an expression vector that expresses a fusion protein according to the invention. The expression vector is, of course, chosen according to the nature of the host cell chosen for expression of the protein. Suitable such expression vectors are available commercially. Expression is preferably carried out in a prokaryotic host, more preferably a microbial host, especially E. coli, when a suitable expression vector is a prokaryotic expression vector such as a bacterial plasmid of pET system provided from Novagen. Co.

Application of the Fusion Protein of the Invention

The invention provides a fusion protein as a delivery vector. The fusion protein of the invention has high efficiency of transfection in vitro and particularly in vivo, which can deliver gene into cells, embryos and living animals. The gene delivery performed by the fusion protein can be performed in species-specific, even individual-specific ways. Therefore, the fusion protein of the invention is an effective tool in the field of gene therapy and the production of transgenic animals.

The following Examples are offered by way of illustration and not by way of limitation.

EXAMPLES

Example 1

Cloning and Construction of the Fusion Protein of the Invention

A single colony of E. coli strain of DH5α was picked up and then added to 100 μl of sterile water. The resulting solution was boiled for 5 minutes. After brief centrifugation, aliquot of 10 μl was taken and used as the DNA template for CspA gene amplification by polymerase chain reaction (PCR). The primer 1 and primer 2 were used to amplify CspA gene from E. coli. The sequence of primer 1 and 2 are listed bellow:

```
Primer 1:
5'-gctagcATGTCCGGTAAAATGACTGGTATCGTAAA-3'

Primer 2:
5'-ctcgagATTACAGGCTGGTTACGTTA-3'
```

(Small letters indicated Nhe I cutting site. Underlined small letters indicated Xho I cutting site)

After 25 cycles of PCR (annealing temperature was set at 55° C. for 1 min), the PCR product was analyzed by 1.2% agarose gel electrophoresis and then purified by QIAquick PCR products Purification Kit (QIAGEN, Co.). The purified PCR products were cloned into pGEM-T vector (Promega Co.) and the screening of recombinant plasmid was instructed by manufacturer's technical manual and the plasmid pGEM (T)/CspA was obtained and then verified by DNA sequencing. Therefore, such cold shock protein A (CspA; Cold shock domain) further modified by inserting the DNA condensation or binding domain in the cold shock domain of the invention is used to bind double stranded nucleic acids.

Fusion Protein I: The simplest form of the fusion protein is comprised by the combination of NLS+/PTD from TAT and CSD, which is referred as rTAT (see FIG. 1). The DNA binding/NLS+/PTD, reversed form of Tat peptide sequence (rTat), was encoded by the following synthetic oligonucleotides:

```
Oligo (1):
5'-taTGGGTCGCCGTCGTCAACGTCGTAAAAAGCGCCGTT-3'

Oligo (2):
5'-ctagAACCGCGCTTTTTACGACGTTGACGACGGCGACCCA-3'
```

Fusion Protein II

Figure 2:
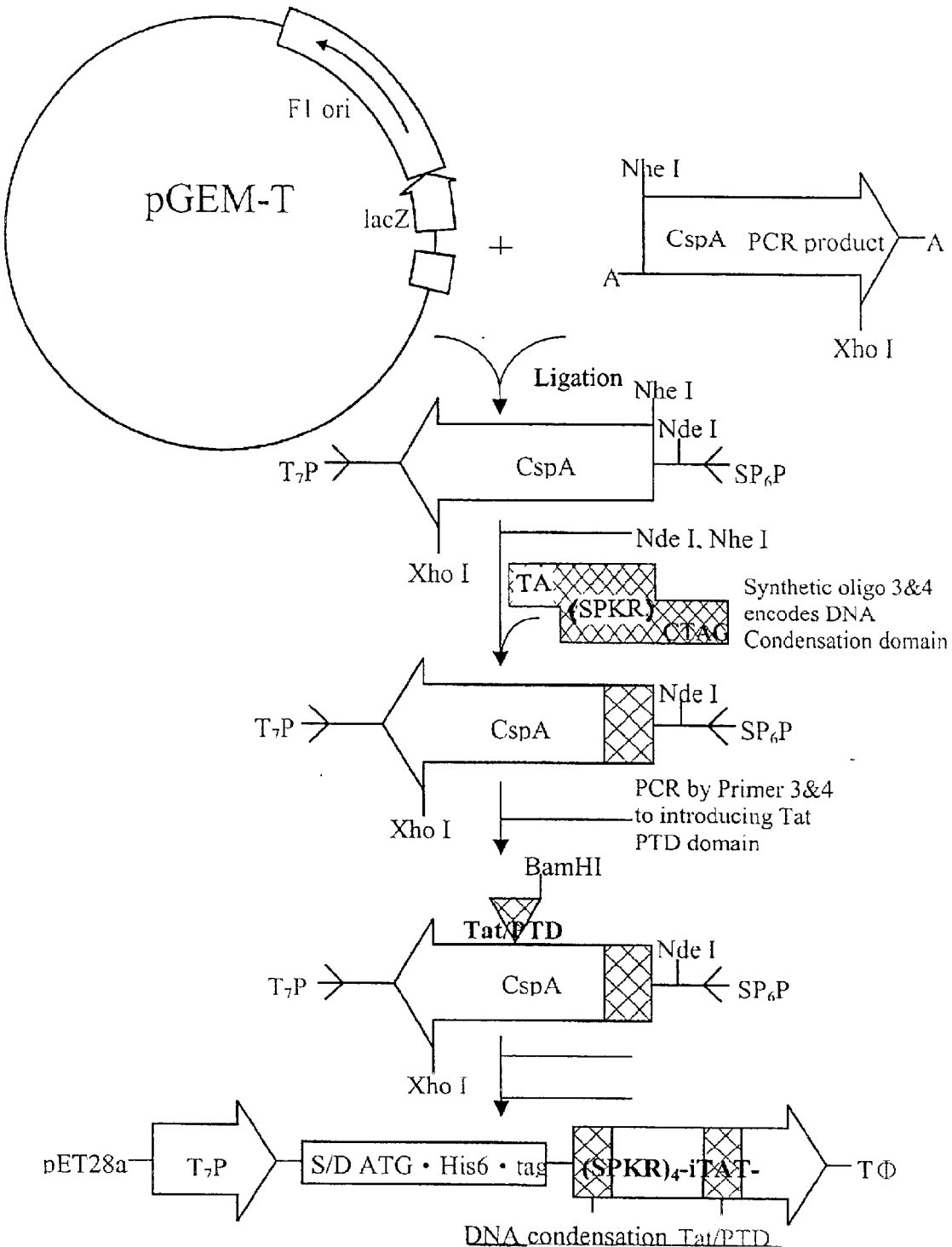
FIG. 2 shows the construction of gene that encodes the fusion protein of invention, (SPKR)4-iTAT-CspA, is represented by simplified flow-chart. The CspA gene is amplified from E. coli by PCR with primer 1 and 2, and gained the double stranded DNA/RNA binding activity by the insertion of annealed synthetic oligo 3 and 4 that encodes DNA condensation sequence (SPKR)4 and the PTD sequence is further introduced into the modified CspA gene by PCR amplification with primer 3 and 4 and then the resulting of modified gene of the invention was subcloned into the pET28a expression vector.

The second form of fusion protein is comprised by the combination of NLS+/PTD from TAT and DNA condensation sequence of (SPKR)4 and CSD, which is referred as (SPKR)4-iTAT-CspA (see FIG. 2). The DNA condensation sequence, (SPKR)4, was encoded by the following synthetic oligonucleotides:

```
Oligo (3):
5'-taTGGGCTCTCCTAAACGCTCTCCTAAACGCTCTCCTAAACGC
TCT CCTAAACGTGGTT-3'

Oligo (4):
5'-ctagAACCACGTTTAGGAGAGCGTTTAGGAGAGCGTTTAGGAG
AG CGTTTAGGAGAGCCCA-3'
```

100 pmol of each of the oligo(1) and oligo(2) or oligo(3) and oligo(4) were mixed separatively and heated at 95° C. for 5 minutes. The annealed double-stranded oligonucleotides were slowly cooled to 4° C. and stored at −20° C. overnight. The 5'-end labeling of annealed double-stranded oligonucleotides were instructed by the manufacturer's recommendation with T4 polynucleotide kinase (purchased from Amersham Co.) and ATP. After 1 hour of incubation at 37° C., the reaction was stopped by heat inactivation and then extracted by phenol:chloroform:isoamyloalcohol (v/v/v=25:24:1; Applichem Co.). The annealed double-stranded oligonucleotides were precipitated by glycogen (Roche Co.) and cold absolute ethanol (Merck Co.).

The synthetic oligonucleotides encode reversed form of Tat peptide sequence (rTat) or DNA condensation sequence (SPKR)4 were cloned into the Nde I, Nhe I-treated pGEM (T)/CspA respectively by T4 DNA ligase (New England Biolab. Conn.) and transformed into E. coli strain DH5α to obtain pGEM (T)/rTAT-CspA and pGEM (T)/(SPKR)4-CspA DNA plasmid, respectively. For further constructing modified (SPKR)4-CspA with membrane translocation activity, we used primer 3 and 4, which were complemented with the partial coding sequence of CspA, and PTD coding sequence from TAT was incorporated into primer 4 and the DNA plasmid pGEM (T)/(SPKR) 4-CspA was used as PCR template. After 25 cycles of PCR, the PTD sequence was introduced into the pGEM (T)/(SPKR) 4-CspA by primer 3 and 4 with Taq enzyme (purchased from Takara. Co.). The sequence of PTD primer 3 and 4 are listed bellow:

```
Primer 3:
5'-NNNNNGGATCCAGAGAAGTGTACGAACACATC-3'

Primer 4:
5'-NNNNNGGATCCCGCAAGAAACGCCGTCAACGCCGCAGAGGATCTCTG
GACGAAGGTCAGAAA.
```

(Underlined letters indicated Bam HI cutting site.)

The annealing temperature is set at 54° C. for 1 minute. After 25 cycles of PCR, the resulting PCR products were purified by QIAquick PCR purification kit and subjected to Dpn I and Bam HI digestion. After the restriction enzyme digestion, DNA was separated onto 1% agarose gel (1×TAE) and purified DNA by QIAquick gel extraction kit (QIAGEN. Co.). The purified DNA was self-ligated and then transformed into E. coli strain DH5α to obtain the pGEM (T)/(SPKR) 4-iTat-CspA plasmid.

Construction of Expression Vector

The fusion protein sequence encoded by the pGEM(T)/rTAT-CspA or (SPKR)4-iTat-CspA plasmids were subjected to NdeI and XhoI digestion and then separated onto 1% agarose gel and excised the DNA fragments containing the coding sequence of rTAT-CspA or (SPKR)4-iTat-CspA fusion protein were used as DNA insert, respectively. Expression vector pET28a (Novagen Co.) was treated with the same restriction enzymes Nde I, XhoI and then ligated with DNA insert rTAT-CspA or (SPKR)4-iTat-CspA fusion proteins coding sequence respectively and then transformed E. coli strain of DH5α to obtain pET28a/rTAT-CspA or pET28a/(SPKR)4-iTat-CspA and then pET expression vectors were subjected to DNA sequencing. The sequencing verified pET28a/rTAT-CspA or pET28a/(SPKR)4-iTat-CspA plasmids were transformed into E. coli strain BL21 (DE3) codon-plus cell (purchased from Stratagene. com) respectively for the expression of fusion proteins of the invention.

Expression and Purification of Fusion Protein of the Invention

E. Coli strain BL21 (DE3) codon-plus cells harboring pET28a/rTAT-CspA or pET28a/(SPKR)4-iTat-CspA plasmids were grown on LB (Kan+, Cm+) plate. A single colony was picked up and inoculated into 2 ml LB broth (Kan+, Cm+) and then incubated at 37° C. for 4 hours. 1 mL aliquot of bacterial culture was inoculated into 400 mL terrific broth (Kan+, Cm+) for further incubation until the optical density OD600 reached 0.6–0.8. The final concentration of 1 mM IPTG were added and then further incubated at 37° C. for 5 to 7 hours. The IPTG-induced E. coli cells were harvested by centrifugation. The resulting pellets were stored at −70° C. in a freezer for further protein purification.

Purification of the Fusion Protein of the Invention

Figure 3:
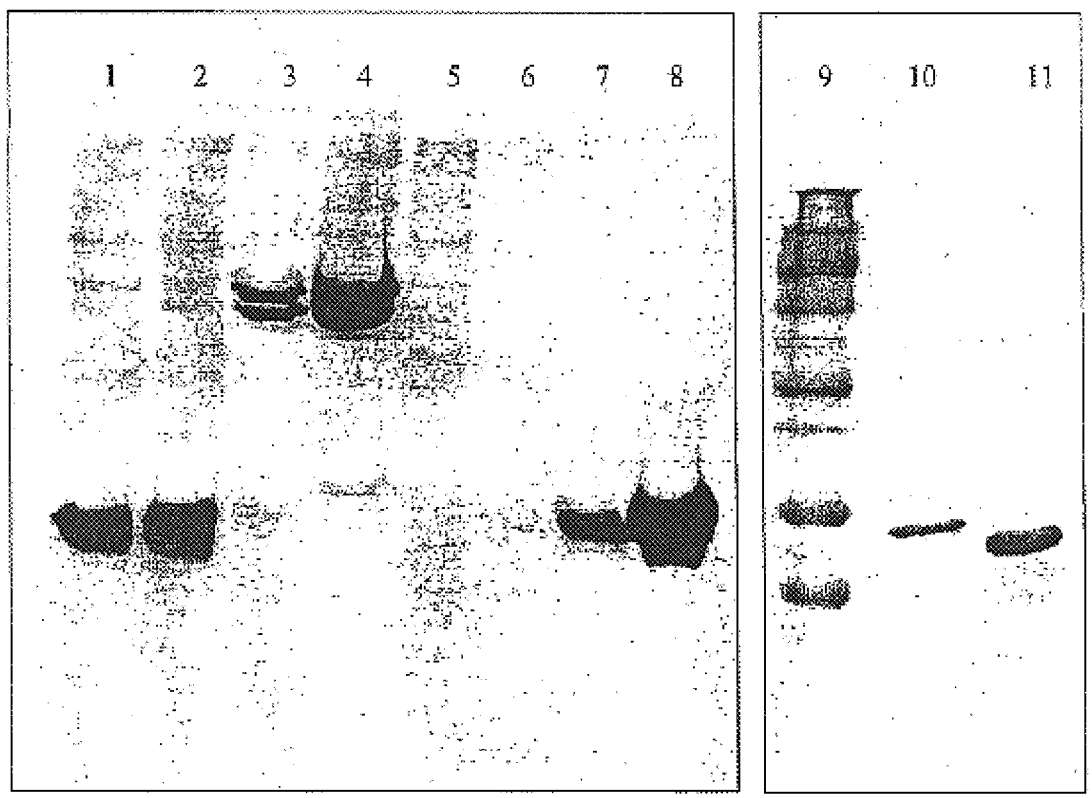
FIG. 3 shows that the induction and purification of the fusion protein is performed by the manufacturer's instruction and purified proteins are analyzed onto the 5%–15% SDS-PAGE and stained gel with coomasie blue; lane 1 is total cell lysate of pET28a/fusion protein; lane 2 is sonicated supernatant 1 of pET28a/fusion protein; lane 3 is sonicated supernatant 2 of pRT28a/fusion protein; lane 4 is sonicated pellets of pET28a/fusion protein; lane 5 is flow through fraction after Nickel-bead affinity column chromatography; lane 6 is wash fraction containing 20 mM imidazole in 1×binding buffer; lane 7 is elution 1 fraction containing; and lane 8 is elution 2 fraction containing 60 mM imidazole in elution buffer; lane 9 is protein molecular weight marker purchased from Amershan-Pharmacia Company; lane 10 is purified iTat protein (0.25 μg); and lane 11 is purified rTat protein (1.0 μg).

The purification of the protein of invention was performed according to the manufacturer's instruction manual of pET system. The IPTG-induced expression E. coli host pellet was resuspended in 1×His Bonding buffer (500 mM NaCl, 20 mM imidazole and 20 mM Tris-Cl, pH 7.9) containing 8M urea, and then disrupted cells by sonication. After ultracentrifugation, the sonicated supernatant fractions were subjected to nickel-ion affinity column and after washing column by 10 volumes of 1×Binding buffer (500 mM NaCl, 25 mM imidazole and 20 mM Tris-Cl, pH 7.9) containing 8M urea and 1×Washing buffer (500 mM NaCl, 40 mM imidazole, 20 mM Tris-Cl, pH 7.9) containing 8M urea. The His6 tagged fusion protein was eluted from the column by 1×elution buffer (500 mM NaCl, 60 mM imidazole, 20 mM Tris Cl, pH 7.9) containing 8M urea. The His6 tagged proteins were dialyzed against 4M urea solution and then steriled $H_2O$. The dialyzed proteins were lyophilized and protein powders were dissolved in 1×PBS solution and the protein concentration was determined by the method of BCA (PIERCE. Co). The purified fusion proteins are analyzed onto the 5% to 15% SDS-PAGE and stained gel with coomassie blue (see FIG. 3). The resulting protein solution was ready for nucleic acid binding assay (gel retardation or EtBr exclusion assay) and test its gene delivery activity.

Example 2
DNA Binding Capacity of Fusion Protein of the Invention

Figure 4:
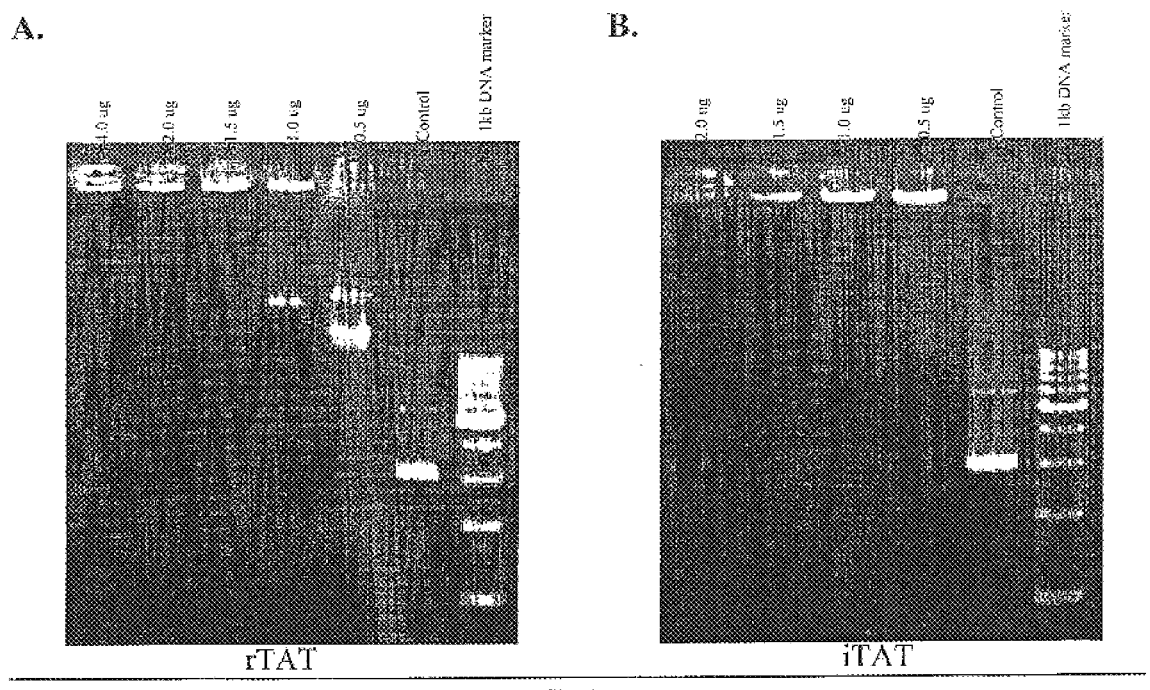
FIG. 4 shows the gel retardation assay. 0.5 μg reporter plasmid pEGFP-N1(purchased from Clontech.com.) was incubated with various amount of protein vector, "rTAT-CspA" or "iTAT-CspA", in the presence of 1×PBS buffer. After incubation at room temperature for 30 min, the DNA-protein complexes were separated onto 1% agarose gel (1×TBE) and stained gel with EtBr.

Briefly speaking, the 0.5 ug reporter plasmid pEGFP-N1 (purchased from Clontech.com.) was incubated with various amount of fusion protein vector rTAT-CspA or (SPKR)4-iTat-CspA in the presence of 1×PBS buffer. After incubation at room temperature for 30 min, the DNA-protein complexes were separated onto 1% agarose gel (1×TBE) and stained with EtBr and photography. Once the large DNA-protein complexes formation, the reporter plasmid DNAs were retarded on the top well of gel by fusion protein binding, therefore could not run into the gel and stain well with EtBr (see FIG. 4).

Figure 5:
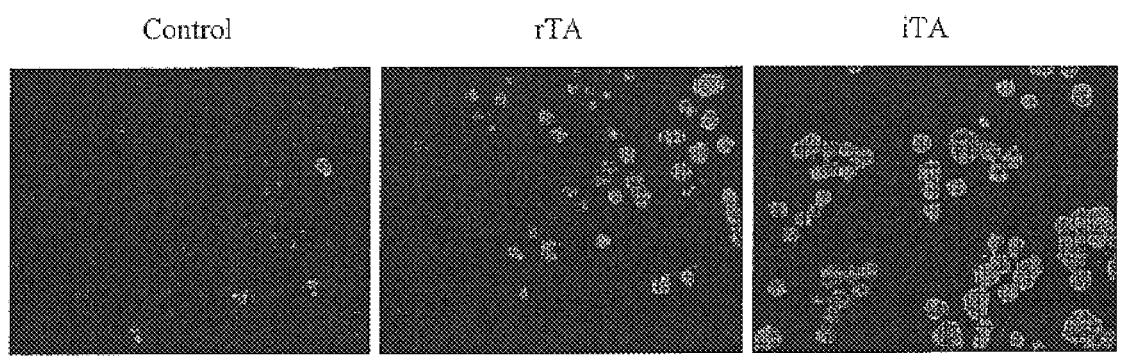
FIG. 5 shows the green fluorescent protein expression from Hela cells that were transfected (1) without DNA plasmid (left panel), (2) rTAT-CspA-pEGFP-N1 complexes (middle), and (3) (SPKR)4-iTAT-CspA-pEGFP-N1. After 1 hours of incubation of DNA-protein complexes with cells, 0.45 mL serum-plus DMEM broth was added and incubated at 37° C. 6 hrs and then 1 mL Serum-plus DMEM broth was added, and the cells were further incubation at 37° C. for 24 hrs and examined the EGFP gene expression by the fluorescent microscope.

Example 3
Transfection of Hela Cells Culture by Fusion Protein Vector and pEGFP-N1 Reporter Plasmid in vitro Subconfluent, monolayer of overnight growth of Hela cells (about $10^6$ cells) plated on the serum-coated cover slip, were washed by 2 times of serum-free DMEM medium and 5 times of 1×PBS buffer gently and then treated cells either with 5 ug reporter plasmid pEGFP-N1 only or the fusion protein (rTat or (SPKR)4-iTat-CspA)-reporter DNA plasmid complexes (5 ug), respectively. Incubation of Hela cells at 37° C. for 1 hour, the 0.45 ml of fresh serum-plus DMEM medium was added and incubation at 37° C. for 6 hours and the 1 ml of fresh serum-plus DMEM medium was added and further incubation. Examination of the transfected Hela cells with the EGFP protein expression directly by fluorescent microscope after 24 hrs incubation (Leica. Co.). As shown in FIG. 5, the Hela cells transfected with the fusion protein-pEGFP-N1 complexes exhibit significant green fluorescent signals in the cells. The results show that the fusion protein of the invention can effectively deliver DNA into cells.

Figure 6:
FIG. 6 shows the green fluorescent protein expression from the fusion protein vector of the invention iTAT-CspA-pEGFP-N1 complexes transfected mouse embryos. The zona-removed mouse embryos were transfected either with 0.75 μg of DNA plasmid pcDNA3.1 (left panel) or the pEGFP-N1 reporter DNA plasmid with protein vector of the invention, iTAT-CspA (right panel), respectively. After the time of intervals of incubation, the mouse embryo were examined the green fluorescent protein expression by the fluorescent microscope.
Figure 6:
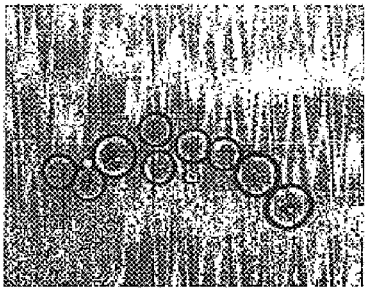
Figure 6:
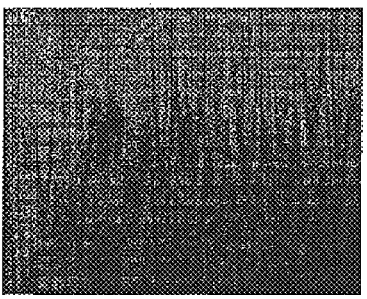
Figure 6:
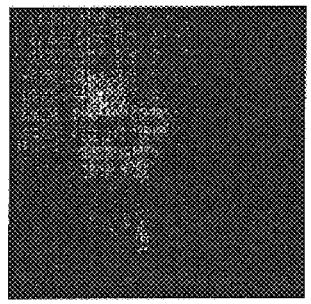

Example 4
Zona-removed Mouse Embryos Transfected by the Fusion Protein of the Invention and pEGFP-N1 Reporter Plasmid in vitro Mouse embryos used for transfection were prepared essentially as described by Gordon, et al (Gordon, J. W., and Ruddle, F. H. (1983). Gene transfer into mouse embryos. Production of transgenic mice by pronuclear injection. Methods in Enzymol., Recombinant DNA, Part C., 101, 411–433.) and Hogan, B., Costantini, F. and Lacy, E. (1986) Manipulating the mouse embryo: A Laboratory Manual). Briefly, the ICR outbred strain purchased from NTU laboratory animal center (Taipei) and then super-ovulated by an injection of 2.5 IU of pregnant mare's serum gonadotrophin purchased from Sigma (G4527), followed 48 hours later by 5 IU of human chorionic gonadotrophin (hCG; Sigma. Co., C8554) and caged individually with ICR males overnight. The one cell of mouse embryos were collected from the oviduct flushing at 24 hours post-hCG injection. Mouse embryos were treated with an aliquot of 0.5% pronase (Sigma. Co., P5147) in M2 medium (Sigma. Co.) for 5 min at 37° C. to remove the zona pellucida and washed gently with M2 medium and 1×PBS buffer several times and then transfected either with control plasmid pcDNA3.1 purchased from invitrogen.com or the Fusion protein vector (SPKR)4-iTat-CspA and reporter pEGFP-N1 plasmid in the condition same as the Hela cells transfection with the exception of 0.75 ug of control plasmid pcDNA3.1 or pEGFP-N1 reporter plasmid was used. After 15 min 37° C. incubation, 1 ml of M16 culture medium (Sigma. Co., M7292) was added and then mounted embryos with mineral oil (Sigma. Com., M8410). At every 24-hours interval of incubation, the embryos were examined the EGFP protein expression by the fluorescent microscope (Leica Co.). As shown in FIG. 6, the fusion protein (SPKR)4-iTat-CspA-pEGFP-N1 reporter plasmid (left) exhibits significant green fluorescent signals in the fluorescent microscopic photograph, which shows that the fusion protein can successfully deliver the DNA pEGFP-N1 reporter plasmid into the embryos.

Figure 7:
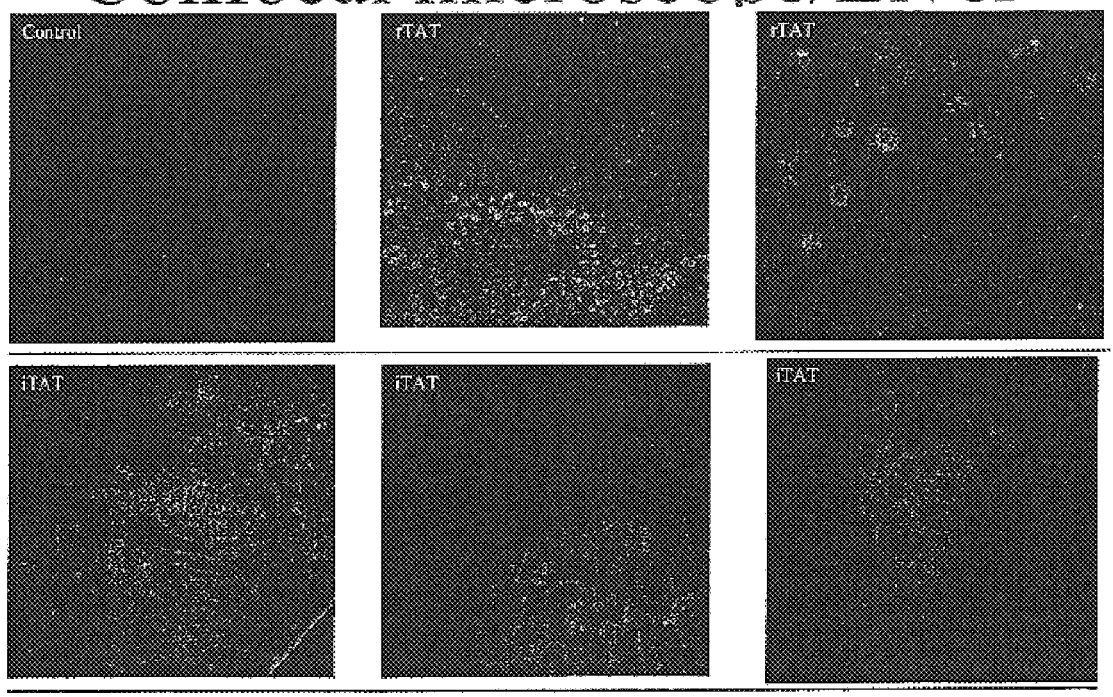
FIG. 7 shows the frozen tissue section of liver, from the mouse treated with the complexes of the protein vector of the invention rTAT- or iTAT-CspA-pEGFP-N1 DNA complexes by i.p. injection. After 48 hr, the mice were sacrificed and then examined the green fluorescent protein expression in the liver by confocal laser scanning microscope (Leica.com.).

Example 5
Delivering Reporter DNA Plasmid pEGFP-N1 into Mouse with the Fusion Protein of the Invention 20 ug of DNA plasmid pEGFP-N 1 was mixed with the fusion protein of the invention rTAT-CspA or (SPKR)4-iTat-CspA in the 1×PBS buffer, incubation at RT° C. for 15 min and then intraperitoneally injected into mouse respectively. 48 hrs later, mice were sacrificed and their livers were subjected to frozen tissue section and then examined EGFP protein expression by the confocal laser scanning microscope (Leica. Co.). FIG. 7 shows that the fusion protein of the invention rTAT-CspA or (SPKR)4-iTat-CspA could successfully deliver the DNA plasmid pEGFP-N1 to the liver cells in vivo.

Example 6
RNA Binding Capacity of Fusion Protein of the Invention

Figure 8:
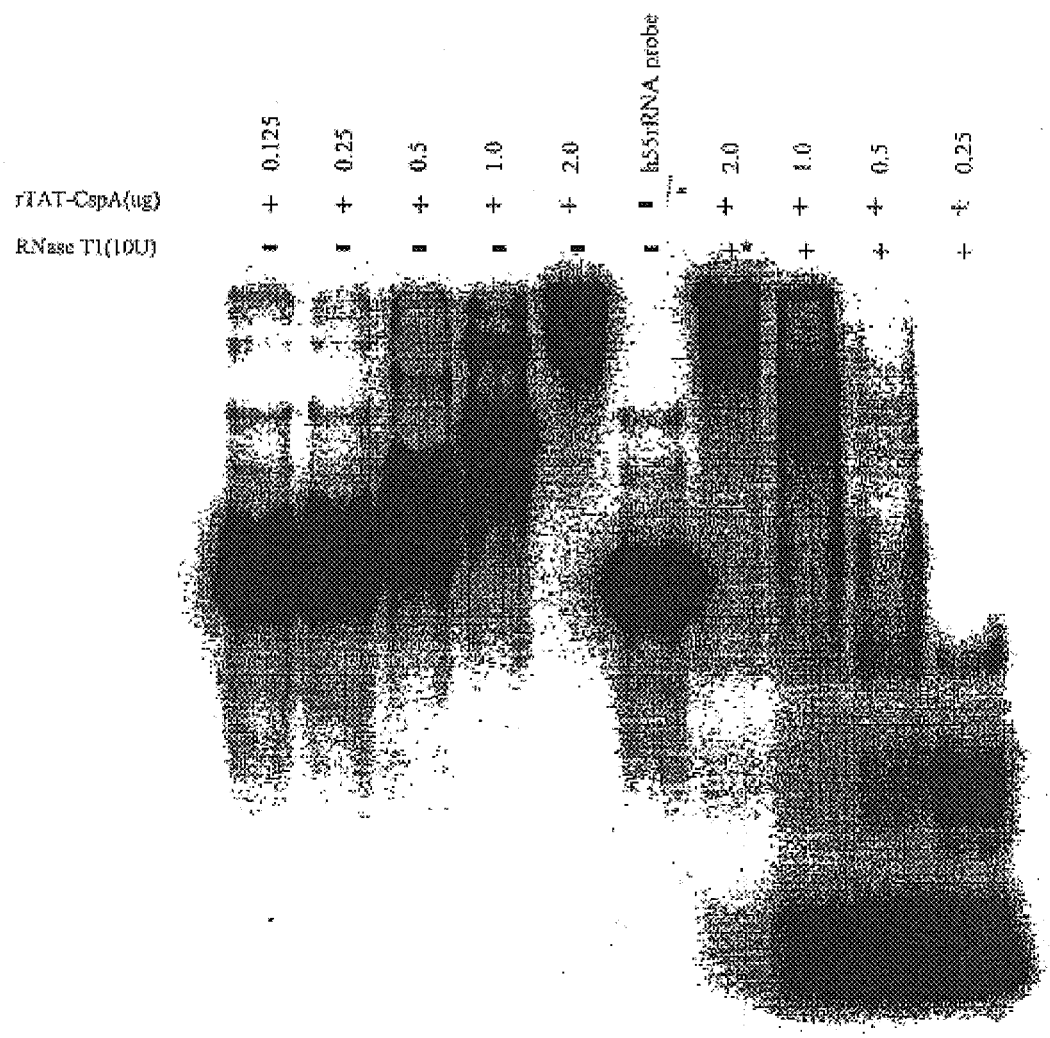
FIG. 8 shows the electrophoretic mobility shift assay (EMSA) being performed by using the protein of the invention, rTAT and human 5S rRNA.

The PCR products of human 5s rDNA were cloned into the pGEM (T) vector. (Promega. Co. A gift from Dr. Elong Lin). The pGEM (T)/h5S rDNA plasmid was digested with Spe I and then separated onto 1% agarose gel (1×TAE). The linear pGEM (T)/h5S rDNA fragments were excited from the agarose gel and purified by QIAquick gel purification kit (QIAGEN. Co.). The human 5S rRNAs were synthesized by using the RiboMAX/T7 large-scale RNA production system (Promega. Co.) and the uniformly labeling of human 5S rRNA with UTP [α-32P] (800 ci/mmol, 10 mCi/mL; NEN. Co.) was performed by the manufacturer's instruction manual. The in vitro synthesized human 5S rRNA was separated onto 12% UREA-PAGE and then purified from the gel by the method of UV shadowing. After ammonia acetate and ethanol precipitation of human 5S rRNA was denatured by heating on the boiled water bath for 5 min and then slowly cooled down to room temperature and stored at −20° C. overnight. 125 ng of human 5S rRNA was mixed with various amount of the protein of invention of rTAT protein, incubation at RT ° C. for 30 min and then treated with or without RNase T1 (10U; Ambion. Co.) for further 10 min incubation at 37° C. The binding complexes were separated into 8% native PAGE (0.5×TBE) and then fixed the gel with 10% acetic of further acid and dry gel and autoradiography. As shown in FIG. 8, the RNase-resistant binding complexes are indicated by symbol "*".

What is claimed is:

1. A fusion protein for delivery of a desired molecule into cells or nuclei, comprising i) a cold shock domain and ii) a membrane translocation sequence.

2. The fusion protein of claim 1, wherein the cold shock domain is selected from the group consisting of CspA, CspB, CspC, CspD, rpl S1 RNA binding domain, eukaryotic Y-box proteins, DNA binding Protein B (DBPB), DBPA, EFE-I, mRNP3, mRNP4, FRG Y1 and nuclease-sensitive-element-binding protein 1 (NSEP 1).

3. The fusion protein of claim 1, wherein the cold shock domain is selected from the group consisting of CspA, rpl S1 RNA binding domain, human YB-1, DNA binding Protein A & B and FRG Y1.

4. The fusion protein of claim 1, wherein the cold shock domain is modified by inserting a DNA condensation domain or a DNA binding domain into the cold shock domain.

5. The fusion protein of claim 4, wherein the DNA condensation or binding domain is selected from the group consisting of DNA condensation domain (SPKR) 3–4 and the positive charge nuclear localization sequences (NLS+).

6. The fusion protein of claim 1, wherein the membrane translocation sequence is a protein transduction domain (PTD) or a membrane fusion sequence.

7. The fusion protein of claim 1, wherein the membrane translocation sequence is a protein transduction domain (PTD) selected from the group consisting of SEQ ID Nos: 1, 2, 3, 4, 5, 6, 7 and 8.

8. The fusion protein of claim 1, wherein the membrane translocation sequence is a protein transduction domain (PTD) selected from the group consisting of SEQ ID Nos: 1, 2, 4, 5, 6 and 7.

9. The fusion protein of claim 1, wherein the membrane fusion sequence is selected from the group consisting of SEQ ID Nos: 9, 10, 11, 12, 13, 14, 15, 16, 17, 18, 19, 20, 21, 22 and 23.

10. The fusion protein of claim 1, wherein the membrane fusion sequence is selected from the group consisting of SEQ ID Nos: 9, 10, 11, 12, 13, 17, 19, 20 and 21.

11. The fusion protein of claim 1, which further comprises a protein purification tagged sequence.

12. The fusion protein of claim 11, wherein the protein purification tagged sequence is selected from the group consisting of haemagglutinin (HA), glutathione-S-transferase (GST), and His6 tag.

13. A fusion protein comprising i) a cold shock domain and ii) a protein transduction domain.

14. The fusion protein of claim 13, which further comprises a protein purification tagged sequence.

15. The fusion protein of claim 14, wherein the protein purification tagged sequence is selected from the group consisting of haemagglutinin (HA), glutathione-S-transferase (GST), and His6 tag.

16. A fusion protein comprising i) a cold shock domain and ii) a membrane fusion sequence.

17. The fusion protein of claim 16, which further comprises a protein purification tagged sequence.

18. The fusion protein of claim 17, wherein the protein purification tagged sequence is selected from the group consisting of haemagglutinin (HA), glutathione-S-transferase (GST), and His6 tag.

19. The fusion protein of claim 16, which further comprises a nuclear localization sequence.

20. The fusion protein of claim 19, which further comprises a protein purification tagged sequence.

21. The fusion protein of claim 20, wherein the protein purification tagged sequence is selected from the group consisting of haemagglutinin (HA), glutathione-S-transferase (GST), and His6 tag.

* * * * *